United States Patent [19]

King

[11] Patent Number: 4,652,635

[45] Date of Patent: Mar. 24, 1987

[54] METHOD FOR CONVERTING ETHER GROUPS TO HYDROXYL GROUPS AND ESTER GROUPS TO ACID GROUPS

[75] Inventor: Patrick F. King, North Quincy, Mass.

[73] Assignee: Polaroid Corporation, Patent Dept., Cambridge, Mass.

[21] Appl. No.: 621,060

[22] Filed: Jun. 15, 1984

Related U.S. Application Data

[63] Continuation-in-part of Ser. No. 490,773, May 2, 1983, abandoned.

[51] Int. Cl.$^4$ ..................... C07C 29/00; C07C 31/04; C07C 37/00; C07F 5/04; C09B 43/00
[52] U.S. Cl. .................... 534/651; 260/502.3; 260/543 B; 534/588; 534/682; 534/726; 548/110; 548/146; 549/4; 549/213; 549/388; 549/394; 549/462; 560/19; 560/37; 560/38; 560/39; 560/41; 562/433; 562/443; 562/444; 562/450; 564/171; 564/174; 568/630; 568/631; 568/644; 568/735; 568/943; 540/128; 540/132; 540/133; 558/291
[58] Field of Search .................... 260/462 R, 162, 163, 260/206, 207, 40.4, 404.5, 543 B, 502.3, 245.74, 245.78, 245.79; 534/588, 651, 682, 726; 548/146, 110; 549/213, 388, 394, 462, 4; 560/19, 37, 38, 39, 41; 562/433, 443, 444, 450; 564/171, 174; 568/630, 631, 644, 735, 943

[56] References Cited

U.S. PATENT DOCUMENTS 2,833,806 5/1958 Hechenbleikner et al. ........ 260/937

OTHER PUBLICATIONS

Boeckman et al., Tetrahedron Letters, vol. 26, No. 11, pp. 1411-1414 (1985).
Gazizov et al., Chemical Abstracts vol. 76 #99263s (1972).
King et al., Tetrahedron Letters, vol. 26, No. 11, p. 1415-1418 (1985).
Steinberg, "Organoboron Chemistry", vol. I, pp. 824-831 (1964).
Williams et al., Tetrahedron Letters, vol. 24, No. 37 pp. 3965-3968 (1983).
Gerard et al., J. Chem. Soc. (London), vol. of 1959, pp. 1529-1535.
Henderson et al., Annual Review of NMR Spectroscopy, vol. 2, pp. 219, 277, and 287 (1969).
Steinberg, "Organoboron Chemistry", vol. I, pp. 341, 554, 555, 844, and 845 (1964).

Primary Examiner—Floyd D. Higel
Attorney, Agent, or Firm—Gaetano D. Maccarone

[57] ABSTRACT

A method for converting ether groups such as alkyl or aryl ether groups including hydroquinone ether groups to hydroxyl groups and ester groups such as alkyl or aryl ester groups to carboxylic acid groups which comprises reacting a compound including at least one ether and/or ester group with a 2-halo-1,3,2-benzodioxaborole to form an intermediate and hydrolyzing the intermediate such as by quenching it into water to form the desired final product.

9 Claims, No Drawings

METHOD FOR CONVERTING ETHER GROUPS TO HYDROXYL GROUPS AND ESTER GROUPS TO ACID GROUPS

CROSS-REFERENCE TO RELATED APPLICATIONS

This application is a continuation-in-part of prior copending application Ser. No. 490,773, filed May 2, 1983, now abandoned.

BACKGROUND OF THE INVENTION

This application relates generally to a chemical synthetic method and, more particularly, to a method for converting ether groups to hydroxyl groups and ester groups to acid groups.

It is known in the art to convert ether groups in compounds to hydroxyl groups by reacting the compound with boron tribromide in a solvent such as methylene chloride, typically at a temperature of $-78°$ C. This reaction has been taught for converting dye developer precursors, which are blocked with ether groups such as methoxy or benzyloxy, to dye developers which are useful in photographic applications.

This reaction is not completely satisfactory because in some instances the borate complex intermediate precipitates from solution before the reaction is complete, thus leading to significantly lower yields of pure product. Raising the temperature to deal with the solubility considerations does not necessarily overcome this disadvantage because boron tribromide is a strong Lewis acid and significant amounts of decomposition products can be encountered at the elevated temperatures.

The present invention is drawn to a method for converting ether groups to hydroxyl groups and ester groups to acid groups which proceeds under mild reaction conditions and which typically involves the formation of soluble intermediates.

SUMMARY OF THE INVENTION

It is therefore an object of this invention to provide a method for converting ether groups to hydroxyl groups and ester groups to acid groups.

It is a further object to provide such a method wherein the intermediate formed is not isolated.

It is a still further object to provide such a method wherein the intermediate formed is typically soluble in the reaction medium.

It is another object to provide such a method which proceeds under mild reaction conditions.

Yet another object is to provide such a method which provides high yields of final product.

Still another object is to provide a method for converting a dye developer precursor to a dye developer which is useful in photographic applications.

BRIEF SUMMARY OF THE INVENTION

These and other objects and advantages are accomplished in accordance with the invention by providing a method wherein a compound which includes at least one ether group and/or at least one ester group is reacted with a 2-halo-1,3,2-benzodioxaborole in a solvent, preferably in the presence of an auxiliary reagent which will increase or decrease reactivity as desired, to form an intermediate which is then hydrolyzed such as by quenching it into water to form the desired final product. The final product is recovered such as by filtration in the case of solids or extraction with an appropriate solvent in the case of non-solids.

It should be understood that by an ether group as used throughout the specification and in the claims, is meant a $$-\overset{|}{\underset{|}{C}}-OR$$

group wherein R can be alkyl, preferably having from 1 to 6 carbon atoms, aralkyl such as benzyl, phenethyl or the like, or aryl such as phenyl, naphthyl or phenyl or naphthyl substituted with substituents such as halogen, sulfonamido, alkyl, etc. By an ester group is meant a $$-\overset{O}{\underset{\|}{C}}OR$$

group wherein R is as defined above.

In the case of compounds which include an ether group the method can be illustrated as follows:

R'OR + [2-BX-1,3,2-benzodioxaborole] ⟶

1         2

R'O—B[1,3,2-benzodioxaborole] + RX

3

3 + $H_2O$ ⟶ R'OH + [catechol (benzene-1,2-diol)] + $H_3BO_3$ wherein R' can be alkyl including straight chain or branched; cycloalkyl such as cyclopentane, cyclohexane or cycloheptane, including substituted cycloalkyl having substituents such as amides, sulfones, etc.; aryl such as 6 member carbocyclic moieties or 5 or 6 member heterocyclic moieties which may include N, S or O atoms; and X is a halogen, preferably bromine or chlorine.

In the case of compounds containing an ester group the method can be illustrated as follows:

R'COR + [2-BX-1,3,2-benzodioxaborole] ⟶

4

R'CX + [2-OR-1,3,2-benzodioxaborole]

5

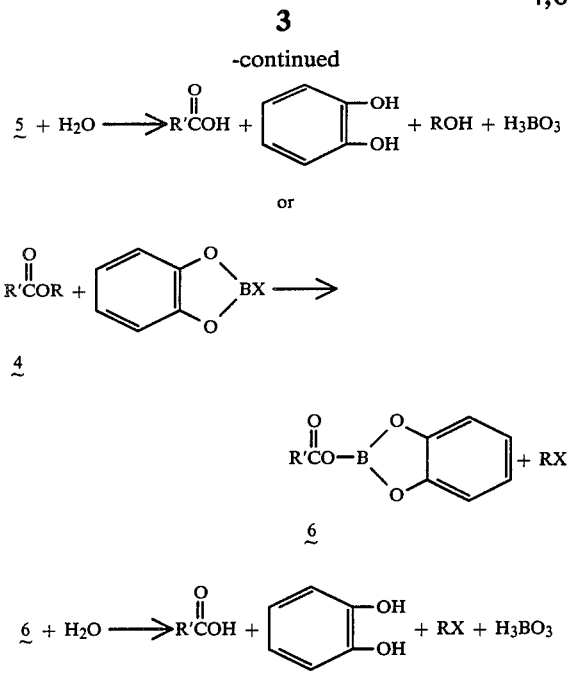

The first reaction sequence tends to be favored when R is aromatic whereas the second reaction sequence tends to be favored when R is other than aromatic such as where R is alkyl.

Referring now to the representation of the ether compound 1 in the illustrations, although R and R' can be the same, with the exception that they cannot both be aryl, it should be recognized that in any compound having at least one ether group which is to be converted to a hydroxyl group in accordance with the method of the invention the R group preferably should be more reactive than R' such that the method affords R'OH as a reaction product. In the case of the ester groups R and R' can be the same.

It should also be understood that in the representation of the ether compound 1 and the ester compound 4, R' is intended to designate, with the exception of —OR, the remainder of the compound and therefore encompasses a great variety of moieties as will become apparent from the detailed description provided herein. For example, R' may simply be one of the groups described above such as an alkyl group and the ether compound to be reacted could be CH$_3$OR or the ester compound could be CH$_3$COOR. R', however, also is intended to designate a large moiety which includes one of the reactive groups described above, for example, a dye moiety which itself includes one or more ether and/or ester groups. In a preferred embodiment of the invention R' is a dye moiety which may include one or more ether groups and together with —OR constitutes a dye developer precursor. In a particularly preferred embodiment the ether compound to be reacted is a dye compound which includes one or more hydroquinone ether groups which can be converted to hydroxyl groups. Such compounds can be illustrated as

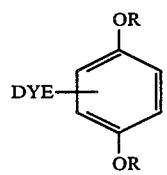

The method of the invention provides an advantageous synthetic procedure for the conversion of ether groups to hydroxyl groups and ester groups to carboxylic acid groups. Since the intermediates formed are typically soluble in the reaction mixture they can be converted in situ to provide high yields of the desired final product. Moreover, the reactions can be carried out under mild conditions which also contributes to high yields of the desired product.

DESCRIPTION OF THE PREFERRED EMBODIMENTS

As described previously, the method of the invention is carried out under mild reaction conditions, preferably at room temperature. The solvent may be any inert organic solvent such as, for example, methylene, chloride, benzene, chloroform or the like. It is preferred to carry out the reaction with about 1.5 equivalents of the benzodioxaborole compound per ether and/or ester group in the starting compound. Undesired side reactions may occur when too great an amount of the benzodioxaborole compound is present.

It is also preferred to carry out the method in the presence of an auxiliary reagent which is used to either increase or decrease the rate of reactivity. Generally, about 1.0 equivalent of an auxiliary reagent per acid site in the starting compound is used. Preferred auxiliary reagents are boron trifluoride etherate which typically accelerates the reaction and pyridine which typically retards the reaction rate slightly.

Typical compounds which may be reacted according to the method of the invention are illustrated by the formulas

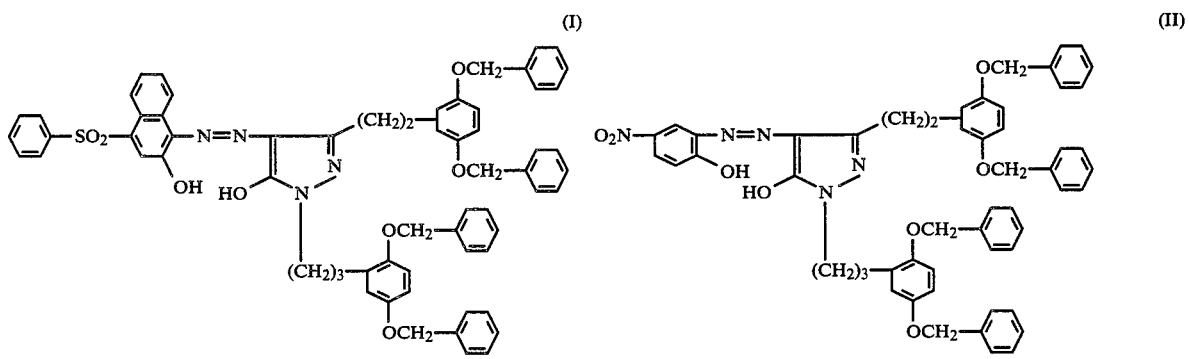

-continued
(III)
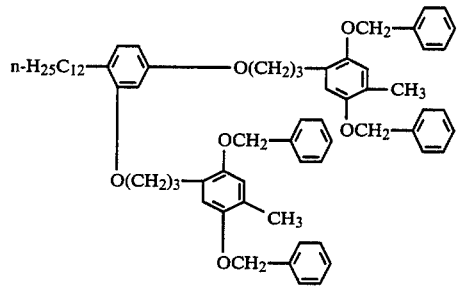
(IV)
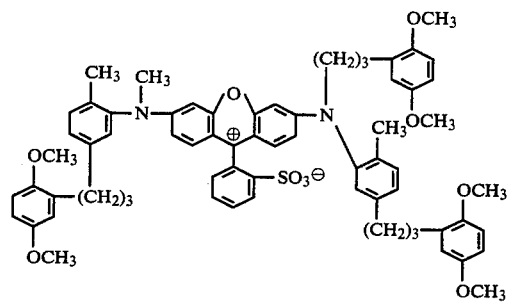
(V)
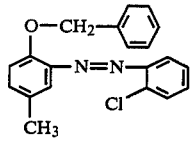
(VI)
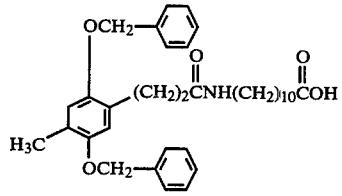
(VII)
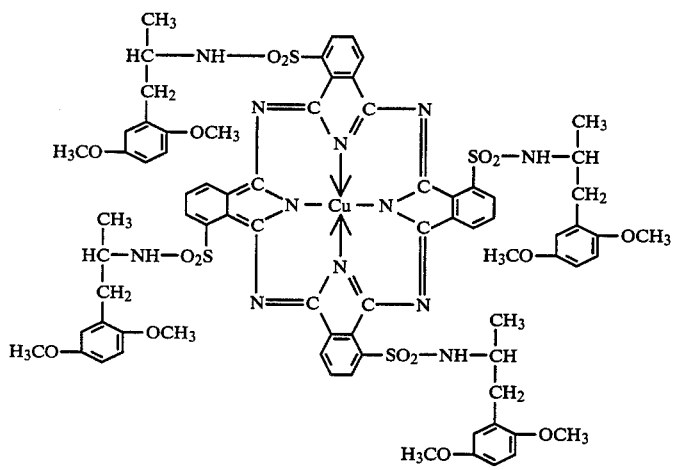
(VIII)
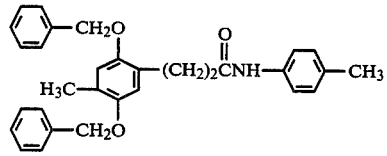
(IX)
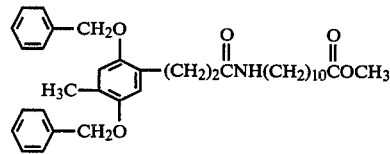
(X)
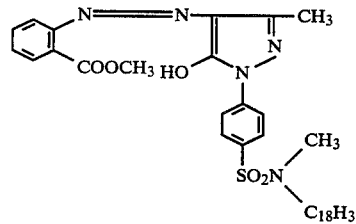
(XI)
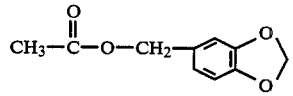
(XII)
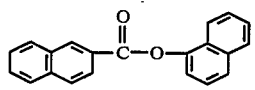
(XIII)
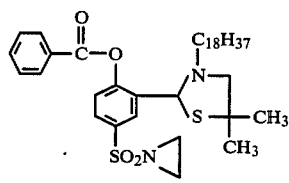

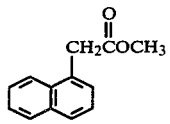

(XIV)

The 2-halo-1,3,2-benzodioxaborole can be made according to reactions which are well known in the art. See, for example, Gerrard et al, J. Chem. Soc. 1959, p 1529. Generally, the compound can be prepared by reacting catechol with boron tribromide in a solvent such as methylene chloride at −78° C.

The invention will now be described further in detail by way of examples, it being understood that these are intended to be illustrative only and the invention is not intended to be limited to the materials, conditions, process parameters, etc. which are recited therein.

EXAMPLE I

Solid catechol (800 gms) was added (via a Gooch tube connected to an Erlenmeyer flask) to a 12 liter round bottom flask containing BBr$_3$ (2 kg) in methylene chloride (3.5 liters) at −78° C. over a 6 hour period. The reaction mixture was slowly warmed to ambient temperature and stirred overnight. The solvent and excess hydrogen bromide were removed by distillation at 20 mm Hg. The residue was transferred in a minimal amount of methylene chloride to a 5 liter three neck round bottom flask and evacuated overnight at 30 mm. At this point the reaction product was very crystalline. The solid was warmed cautiously to a melt while slowly reducing the pressure. Ultimately, at a pressure of 10–15 mm an a mantle temperature of about 130° C., there was formed a colorless distillate at a head temperature of about 95° C. The liquid crystallized rapidly on cooling. The solid was transferred to Teflon bottles to yield 1.32 kg (92% yield) of 2-bromo-1,3,2 benzodioxaborole, a colorless, fuming, pourable solid.

$^{11}$B NMR (CDCl$_3$; BF$^-_4$ external) δ24.66.

EXAMPLE II

To a solution of boron trifluoride etherate (27 gms) and 2-bromo-1,3,2-benzodioxaborole (200 gms) in 2 liters of methylene chloride there was added, rapidly at room temperature with stirring, a solution of compound I (100 gms) in 1 liter of methylene chloride. The reaction was followed by thin layer chromatography. After one hour the reaction appeared to be complete. The reaction mixture was quenched into four gallons of cool water including 1 gm of ascorbic acid with stirring followed by the addition of one-half gallon of hexane. The mixture was stirred for fifteen minutes and then filtered. The residue was washed well with water and then with hexane and dried under vacuum to give 70 g of crude dye developer. The crude dye developer was recrystallized from hot acetic acid (10 g/100 ml) to yield 56 g of pure dye developer (82% yield).

Vis. (Me Cell) λ max 475 nm, ε=22,000.

C$_{36}$H$_{36}$N$_4$O$_8$S requires 63.2%C, 4.7%H, 8.2%N and 18.7%O. Elemental analysis found 63.4%C, 4.98%H, 7.9%N and 18.4%O.

EXAMPLE III

A solution of compound I (1 gm) in 20 ml of methylene chloride was added dropwise at room temperature to a solution of 2-bromo-1,3,2-benzodioxaborole (2 gms) in 100 ml of methylene chloride. The solution turned a magenta color immediately. Analysis by thin layer chromatography showed conversion of the benzyl groups to hydroxyl groups. The reaction mixture was poured into ethanol and the solution was extracted with ethyl acetate. The organic extract was washed with water, dilute HCL and saline solution, dried over calcium sulfate and then evaporated to dryness to yield 0.6 g.

The structure of the product was confirmed by thin layer chromatography and a visible spectrum which were identical to those of the product of Example II.

EXAMPLE IV

To a solution of compound II (10 gms) in 600 ml of methylene chloride there were added boron trifluoride etherate (1.6 g) followed by 2-bromo-1,3,2-benzodioxaborole (20 gms) and the mixture was stirred for twelve hours. The reaction was deemed complete by reverse phase thin layer chromatography. The reaction mixture was quenched into water which was stirred for about one-half hour. The solid was collected, washed with water and then with hexane and dried under vacuum to give 4.5 gms (85% yield) of the dye developer.

Vis (Me Cell) λ max 410 nm, ε=14,700.

The structure of the product was confirmed by a proton NMR spectrum.

EXAMPLE V

A solution of compound II (1 gm) in 30 ml of methylene chloride was added dropwise to a refluxing solution of 2-bromo-1,3,2-benzodioxaborole (10 g) in 50 ml of methylene chloride. The reaction was complete after about one-half hour as indicated by thin layer chromatography. The reaction mixture was quenched into 500 ml of water which was then stirred for about one-half hour. The solid was collected, washed with water and then with hexane and dried under vacuum to give 0.5 g (85% yield) of the dye developer.

The structure of the product was confirmed by thin layer chromatography and a visible spectrum which were identical to those of the product of Example IV.

EXAMPLE VI

To a solution of compound VII, (75 gms) in 2 liters of methylene chloride there was added, at room temperature, a solution of boron trifluoride etherate (27 gms) in 300 ml of methylene chloride. The solution turned deep green. To this solution there was added, all at once with stirring at room temperature, a solution of 2-bromo-1,3,2-benzodioxaborole (200 g) in 1 liter of methylene chloride. The reaction was followed by thin layer chromatography. After 1½ hours the reaction was nearly complete. The reaction was continued for an additional 36 hours during which time the reaction mixture remained homogeneous. The reaction mixture was quenched into 3 gallons of water and 1 liter of hexane under nitrogen. The solid was collected by filtration, rinsed with hexane and water, redispersed in 3 gallons of water under nitrogen and collected again. The solid was allowed to dry in air for three days and then dried under vacuum at 40° C. to give 69.5 g (98% yield) of the dye developer.

Vis (Me Cell) λ max 673 nm, ϵ=182,000.

$C_{68}H_{60}O_{16}N_{12}S_4Cu$ requires 54.69%C, 4.02%H, 17.16%O, 11.26%N, 8.58%S and 4.25%Cu. Elemental analysis found 54.09%C, 4.40%H, 16.51%O, 11.23%N and 8.57%S.

The structure of the dye developer was further confirmed by thin layer chromatography and a visible spectrum which were identical to those of a known sample of the dye developer which had been prepared by a known alternate method.

EXAMPLE VII

A solution of 2-bromo-1,3,2-benzodioxaborole (200 gms) in 1 liter of methylene chloride was added to a solution of compound IV (92 gms) and boron trifluoride etherate (27 gms) in 2.5 liters of methylene chloride and stirred overnight. An additional 100 gms of the borole compound was added to the reaction mixture and it was stirred for an additional 24 hours. The reaction mixture was quenched into 4 gallons of distilled water (deaerated and containing 5 gms of ascorbic acid). The solid was collected, dried in air and redissolved in 600 ml of methyl cellosolve containing 1 g of ascorbic acid. The solution was filtered through diatomaceous earth to remove insoluble material. The solid was precipitated from solution by quenching into water, collected and dried under vacuum to yield 61 g of dye developer (72% yield).

Vis (Me Cell) λ max 553 nm, ϵ=109,000.

The structure of the dye developer was confirmed by thin layer chromatography and a visible spectrum which were identical to those of a known sample of the dye developer which was made by a known alternate method.

EXAMPLE VIII

A solution of 2-bromo-1,3,2-benzodioxaborole in 1.5 ml of deutero methylene chloride was prepared. After 12 hours a small amount of compound V was added to the solution. This NMR experiment demonstrated the stability of the borole reagent with time. Quenching of the reaction mixture in water after 2 hours yielded the deblocked dye.

Vis (Me Cell) λ max 441 nm, ϵ=7,800. The visible spectrum was identical to that of a known sample of the dye which had been prepared by a known alternate method.

EXAMPLE IX

Boron trifluoride etherate (7.66 g, 6.6 ml) was added to a solution of compound VIII (25 g) in 200 ml of methylene chloride with stirring under nitrogen followed by 23.6 g of 2-bromo-1,3,2-benzodioxaborole. After stirring for one hour, an additional 5 g of the borole compound were added and stirring continued for one hour more. Thin layer chromatographic analysis showed the reaction to be complete. The reaction mixture was quenched slowly into 2 liters of water with stirring. An oily white precipitate formed. A liter of petroleum ether was added and the mixture stirred for one-half hour while bubbling nitrogen through. The resulting white solid was collected and washed well with water and petroleum ether. The solid was recrystallized from 400 ml of 2-propanol and dried under vacuum to give 8.4 g (55% yield) of the dye developer.

The structure of the product was confirmed by a $^{13}CNMR$ spectrum. $^{13}CNMR$ (CDCl$_3$, TMS) δ170.73, 117.60, 117.20, 136.77, 131.82, 128.96, 124.92, 121.81, 119.19, 117.19, 116.09, 36.67, 25.50, 20.35, 15.77.

$C_{17}H_{19}O_3N$ requires 71.56%C, 6.71%H, 16.82%O and 4.91%N. Elemental analysis found 71.87%C, 6.9%H, 16.98%O and 4.8%N.

EXAMPLE X

A solution of 2-bromo-1,3,2-benzodioxaborole (1 g) in methylene chloride was added to a solution of compound IX (0.5 g) in 30 ml of methylene chloride with stirring at room temperature. The reaction mixture was stirred overnight. Thin layer chromatography indicated ether cleavage only after 15 minutes as compared with a known sample prepared with a known alternate method. Thin layer chromatography indicated complete reaction after 12 hours with both ester and ether cleavage with the amide intact and 0.2 g of the deblocked product was isolated. The structure of the product was confirmed by thin layer chromatography and a proton NMR spectrum which were identical to those of a known sample prepared by a known alternate method. $^1H$ NMR (CDCl$_3$, TSM) δ8.65 (2H) 6.8 (1H), 6.55 (1H), 6.45 (1H), 2.0–3.1 (8H), 2.1 (3H), 0.7–1.8 (16H).

EXAMPLE XI

Compound IV (15 g) was added to a solution of 29.8 g of 2-bromo-1,3,2-benzodioxaborole in methylene chloride at room temperature with stirring. The reaction mixture was quenched into 3 liters of water containing ½ liter of hexane with stirring. The solid was collected by filtration and dried under vacuum to yield 8.6 g (95% yield). The structure of the dye developer was confirmed by thin layer chromatography and a visible spectrum which were identical to those of a known sample of the dye developer which had been prepared by a known alternate method.

EXAMPLE XII

To a solution of compound X (50 mg) in methylene chloride (2 ml) there was added 75 mg of 2-bromo-1,3,2-benzodioxaborole with stirring. The solution was stirred overnight and quenched into a stirred mixture of 25 ml of ice water and 15 ml of petroleum ether. A yellow-orange solid formed at the liquid interface. The mixture was stirred for 30 minutes and the solid collected by filtration, washed successively with water and petroleum ether and dried in air to give 45 mg (92% yield) of product.

The structure of the product was confirmed by thin layer chromatography and a proton NMR spectrum which were identical to those of a known sample prepared by a known alternate method.

$^1H$ NMR (D$_6$ DMSO/CDCl$_3$; TSM) δ14.75 (1H, s), 7.0–8.3 (8H, m), 2.98 (2H, t), 2.7 (3H, s), 2.36 (3H, s), 0.8–1.8 (35H, m).

EXAMPLE XIII

To a solution of 3,4-methylenedioxybenzylacetate, compound XI, (1 g) in methylene chloride (30 ml) there was added 2-bromo-1,3,2-benzodioxaborole (1 g) and the mixture stirred for 2 mixtures at ambient temperature. The reaction mixture was quenched into 200 ml of a 1:1 (V/V) mixture of petroleum ether and water. The organic phase was washed twice with 100 ml volumes of water and then with saline solution and dried over calcium sulfate. Removal of the solvent gave 0.93 g (84% yield) of a white solid.

The structure of the product was confirmed by thin layer chromatography and proton NMR which were identical to those of a known sample prepared by a known alternate method.

EXAMPLE XIV

To a solution of 2-naphthyl-1-naphthylene carboxylate, compound XII, in methylene chloride (30 ml) there was added 2 g of 2-bromo-1,3,2-benzodioxaborole and the mixture stirred for 24 hours at ambient temperature. The reaction mixture was quenched into 200 ml of a 1:1 (V/V) mixture of water and petroleum ether. The phases were separated and an equimolar mixture of 1-naphthyl carboxylic acid and 2-naphthol crystallized from the organic solution to yield 0.8 g of a white solid mixture. On filtration and drying the mixture was resolved by column chromatography on silica gel to give 0.3 g of the acid and 0.32 g of the naphthol.

The structure of the acid was confirmed by thin layer chromatography and proton NMR which were identical to those of a known sample prepared by a known alternate method.

EXAMPLE XV

To a solution of compound XIII (200 mg) in 3 ml of methylene chloride there was added, under nitrogen and with stirring, 150 mg of 2-bromo-1,3,2-benzodioxaborole and stirring continued under nitrogen at room temperature. Thin layer chromatography showed complete reaction after 15 minutes. The reaction mixture was quenched into a stirred solution of 75 ml of water and 25 ml of hexane. The mixture was stirred overnight during which time the organic solvents evaporated leaving a yellowish oil in the water. The oil was extracted with two 15 ml portions of methylene chloride and the organic layer dried over sodium sulfate, then filtered and evaporated leaving a yellow oil which solidified to a glass when evacuated.

The glass was dissolved with about 3 ml of refluxing hexane. Upon cooling to room temperature the product crystallized from solution. The product was collected, washed with about 5 ml of cold hexane and dried in air to give 0.12 g (71% yield) of a slightly yellow solid.

The structure of the product was confirmed by thin layer chromatography and a proton NMR spectrum which were identical to those of a known sample prepared by a known alternate method. $^1$H NMR (D$_6$DMSO/CDCl$_3$; TMS) δ11.9 (1H, bs), 6.8–7.8 (3H, m), 5.0 (1H, s), 3.35 (1H, d), 2.3 (4H, s), 2.1–2.9 (3H, s), 0.7–1.8 (41H, m).

EXAMPLE XVI

To a solution of compound (XIV), methyl-1-naphthalene acetate, (1 g) in 30 ml of methylene chloride there was added 3 g of 2-bromo-1,3,2-benzodioxaborole and the mixture stirred for 24 hours at ambient temperature. The reaction mixture was quenched into 200 ml of a 1:1 (V/V) mixture of water and petroleum ether. The organic phase was washed twice with 100 ml volumes of water, then with saline solution followed by dilution with 100 ml of ether and dried over calcium sulfate. Removal of the solvent gave 0.6 g (64% yield) of a white solid.

The structure of the product was confirmed by thin layer chromatography and a proton NMR spectrum which were identical to those of a sample prepared by a known alternate method.

Although the invention has been described with respect to specific preferred embodiments, it is not intended to be limited thereto, but rather those skilled in the art will recognize the variations and modifications may be made therein which are within the spirit of the invention and the scope of the appended claims.

What is claimed is:

1. A method for converting an ether group to a hydroxyl group or an ester group to an acid group comprising reacting a compound which has at least one

group or at least one

group or both, wherein R is alkyl, aralkyl or aryl, provided that in the case of

when R is Aryl,

is not part of an aryl group, with a 2-halo-1,3,2-benzodioxaborole in an organic solvent to form an intermediate and hydrolyzing said intermediate whereby said

group is converted to a

group and said

group is converted to a

group.

2. The method as defined in claim 1 wherein said reaction is carried out in the presence of an auxiliary reagent which is used to either increase or decrease the rate of reactivity.

3. The method as defined in claim 2 wherein said auxiliary reagent is boron trifluoride etherate.

4. The method as defined in claim 2 wherein said auxiliary reagent is pyridine.

5. The method as defined in claim 1 wherein R is methyl or benzyl.

6. The method as defined in claim 1 wherein said 2-halo-1,3,2-benzodioxaborole is 2-bromo-1,3,2-benzodioxaborole.

7. The method as defined in claim 1 wherein said step of hydrolyzing said intermediate is carried out by quenching said intermediate into water.

8. The method as defined in claim 1 wherein said compound has at least one

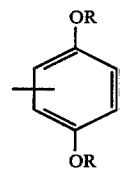

group and is a dye developer precursor.

9. The method as defined in claim 1 wherein said intermediate is soluble in said solvent.

* * * * *